(12) United States Patent
Wang et al.

(10) Patent No.: US 11,096,742 B2
(45) Date of Patent: Aug. 24, 2021

(54) IRRIGATED ABLATION ELECTRODE HAVING SMOOTH EDGES TO MINIMIZE TISSUE CHAR

(71) Applicant: St. Jude Medical, Atrial Fibrillation Division, Inc., St. Paul, MN (US)

(72) Inventors: Huisun Wang, Maple Grove, MN (US); Sacha C. Hall, Westborough, MA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 91 days.

(21) Appl. No.: 16/195,575

(22) Filed: Nov. 19, 2018

(65) Prior Publication Data

US 2019/0231419 A1    Aug. 1, 2019

Related U.S. Application Data

(63) Continuation of application No. 12/346,634, filed on Dec. 30, 2008, now Pat. No. 10,130,418, which is a
(Continued)

(51) Int. Cl.
*A61B 18/14* (2006.01)
*A61B 18/00* (2006.01)

(52) U.S. Cl.
CPC .............. *A61B 18/1492* (2013.01); *A61B 2018/00035* (2013.01); *A61B 2018/00101* (2013.01);
(Continued)

(58) Field of Classification Search
CPC combination set(s) only.
See application file for complete search history.

(56) References Cited

U.S. PATENT DOCUMENTS 4,682,596 A    7/1987  Bales et al.
4,904,238 A    2/1990  Williams
(Continued)

FOREIGN PATENT DOCUMENTS

EP    0667126 B1    3/1999
JP    H09 94296 A    4/1997
(Continued)

OTHER PUBLICATIONS

Author: Wittkampf et al. Title: "Saline-Irrigated Radiofrequency Ablation Electrode with External Cooling" Citation: Journal of Cardiovascular Electrophysiology, vol. 16, No. 3 Publication date: Mar. 2005.
(Continued)

*Primary Examiner* — Scott J Medway
(74) *Attorney, Agent, or Firm* — Dykema Gossett PLLC

(57) ABSTRACT

The invention relates to ablation catheter electrodes that solve in part the problem of tissue charring during radiofrequency ablation. The electrode assemblies of the invention include passageways that lead from the inner lumen of the assemblies to the surface of the assemblies, wherein the passageways have a smooth conjunction with the outer surface. These smooth conjunctions comprise rounded edges or are chamfered. In the case of rounded edges, the rounded edges can have fixed radii of about 0.002" to about 0.008".

8 Claims, 8 Drawing Sheets

Related U.S. Application Data continuation-in-part of application No. PCT/US2007/080920, filed on Oct. 10, 2007.

(60) Provisional application No. 60/828,955, filed on Oct. 10, 2006.

(52) U.S. Cl.
CPC ............... *A61B 2018/00791* (2013.01); *A61B 2018/1472* (2013.01)

(56) References Cited

U.S. PATENT DOCUMENTS

| | | | |
|---|---|---|---|
| 5,056,517 A | 10/1991 | Fenici | |
| 5,230,349 A | 7/1993 | Langberg | |
| 5,348,554 A | 9/1994 | Imran et al. | |
| 5,403,311 A | 4/1995 | Abele et al. | |
| 5,421,819 A * | 6/1995 | Edwards | A61B 18/1485 604/22 |
| 5,423,811 A | 6/1995 | Imran et al. | |
| 5,431,168 A | 7/1995 | Webster | |
| 5,462,521 A | 10/1995 | Brucker et al. | |
| 5,542,915 A | 8/1996 | Edwards et al. | |
| 5,545,161 A | 8/1996 | Imran | |
| 5,584,872 A | 12/1996 | LaFontaine et al. | |
| 5,643,197 A | 7/1997 | Brucker et al. | |
| 5,658,278 A | 8/1997 | Imran et al. | |
| 5,676,693 A | 10/1997 | LaFontaine | |
| 5,792,140 A | 8/1998 | Tu et al. | |
| 5,814,029 A | 9/1998 | Hassett | |
| 5,843,152 A | 12/1998 | Tu et al. | |
| 5,913,856 A | 6/1999 | Chia et al. | |
| 5,919,188 A | 7/1999 | Shearon et al. | |
| 5,971,968 A | 10/1999 | Hata et al. | |
| 6,017,338 A | 1/2000 | Brucker et al. | |
| 6,120,476 A | 9/2000 | Fung et al. | |
| 6,141,576 A | 10/2000 | Littman et al. | |
| 6,162,219 A | 12/2000 | Nilsson et al. | |
| 6,168,594 B1 | 1/2001 | LaFontaine et al. | |
| 6,171,275 B1 | 1/2001 | Webster | |
| 6,217,576 B1 | 4/2001 | Tu et al. | |
| 6,238,393 B1 | 5/2001 | Mulier et al. | |
| 6,363,937 B1 | 4/2002 | Hovda et al. | |
| 6,383,144 B1 | 5/2002 | Mooney et al. | |
| 6,602,242 B1 | 8/2003 | Fung et al. | |
| 6,611,699 B2 | 8/2003 | Messing | |
| 7,166,105 B2 | 1/2007 | Mulier et al. | |
| 7,458,142 B2 | 12/2008 | Haindl | |
| 7,485,092 B1 | 2/2009 | Stewart et al. | |
| 7,815,635 B2 | 10/2010 | Wittkampf et al. | |
| 7,857,810 B2 | 12/2010 | Wang et al. | |
| 2002/0087156 A1 | 7/2002 | Maguire et al. | |
| 2003/0212394 A1 | 11/2003 | Pearson et al. | |
| 2004/0054272 A1 | 3/2004 | Messing | |
| 2004/0260280 A1 | 12/2004 | Sartor | |
| 2005/0065511 A1 * | 3/2005 | Geistert | A61B 18/1492 606/41 |
| 2005/0177151 A1 | 8/2005 | Coen et al. | |
| 2006/0184165 A1 | 8/2006 | Webster et al. | |
| 2007/0156128 A1 | 7/2007 | Jimenez | |
| 2007/0156131 A1 | 7/2007 | Datta | |
| 2007/0270791 A1 | 11/2007 | Wang et al. | |
| 2007/0288075 A1 * | 12/2007 | Dowlatshahi | A61B 18/04 607/105 |
| 2009/0093810 A1 | 4/2009 | Subramaniam et al. | |
| 2009/0259222 A1 | 10/2009 | Wang et al. | |

FOREIGN PATENT DOCUMENTS

| | | |
|---|---|---|
| JP | H11-262530 A | 9/1999 |
| WO | 199956812 A2 | 11/1999 |
| WO | 2000067832 A2 | 11/2000 |
| WO | 2005048858 A1 | 6/2005 |
| WO | 2005112814 A2 | 12/2005 |
| WO | 2007136979 A2 | 11/2007 |
| WO | 2008045925 A2 | 4/2008 |

OTHER PUBLICATIONS

Author: Tennyson Smith Title: "The Hydrophilic Nature of a Clean Gold Surface" Citation: Journal of Colloid and Interface Science, vol. 5, No. 1; pp. 51-55 Publication date: May 1, 1980.

Author: Wittkampf et al. Title: "Radiofrequency ablation with a cooled porous electrode catheter" Citation: JACC vol. 11, No. 2, 17a Publication date: Feb. 1988.

\* cited by examiner

IRRIGATED ABLATION ELECTRODE HAVING SMOOTH EDGES TO MINIMIZE TISSUE CHAR

CROSS-REFERENCE TO RELATED APPLICATIONS

The present application is a continuation of U.S. Non-Provisional Utility patent application Ser. No. 12/346,634, filed 30 Dec. 2008 (the '634 application), now U.S. Pat. No. 10,130,418, issued 20 Nov. 2018 (the '418 patent), which is a continuation-in-part of international patent application no. PCT/US2007/080920, filed 10 Oct. 2007 and published in English on 17 Apr. 2008 under international publication no. WO 2008/045925 A2 (the '920 application), designating the United States of America, which claims priority to U.S. Provisional Utility patent application Ser. No. 60/828,955, filed 10 Oct. 2006 (the '955 application). The '634 application, the '920 application, and the '955 application are all hereby incorporated by reference as though fully set forth herein.

BACKGROUND OF THE INVENTION a. Field of the Invention

The present invention relates to irrigated catheter assemblies. The present invention further relates to ablation electrodes and assemblies, including electrode assemblies having distal irrigation fluid flow. The present invention further relates to ablation electrode assemblies having at least one temperature sensing device and a mechanism for irrigating the ablation assembly and targeted areas. The present invention further relates to methods for improved assembly and accurate measurement and control of the electrode temperatures while effectively irrigating the device and target areas.

b. Background Art

Electrical stimulation of myocardial tissue controls the pumping action of the heart. Stimulation of this tissue in various regions of the heart is controlled by a series of conduction pathways contained within the myocardial tissue. In a healthy heart, contraction and relaxation of the heart muscle (myocardium) occur in an organized fashion as electrochemical signals pass sequentially through the myocardium from the sinoatrial (SA) node, which consists of a bundle of unique cells disposed in the wall of the right atrium, to the atrioventricular (AV) node, and then into the left and right ventricles via a route that includes the His-Purkinje system. The AV node is located near the ostium of the coronary sinus in the interatrial septum in the right atrium. Each cell membrane of the SA node has a characteristic tendency of a gradual leak of sodium ions over time leading to a periodic break down of the cell membrane periodically, thus allowing an inflow of sodium ions, and thereby causing the SA node cells to depolarize. The SA node cells are in communication with the surrounding atrial muscle cells such that the depolarization of the SA node cells causes the adjacent atrial muscle cells to also depolarize. This depolarization results in atrial systole, during which the atria contract to empty and fill blood into the ventricles. The AV node detects the atrial depolarization from the SA node and, in turn, relays the depolarization impulse into the ventricles via the bundle of His and Purkinje fibers following a brief conduction delay. The His-Purkinje system begins at the AV node and follows along the membranous interatrial septum toward the tricuspid valve through the AV septum and into the membranous interventricular septum. At about the middle of the interventricular septum, the His-Purkinje system splits into right and left branches, which straddle the summit of the muscular part of the interventricular septum.

Abnormal rhythms generally referred to as arrhythmia can occur in the heart. Cardiac arrhythmias arise when the pattern of the heartbeat is changed by abnormal impulse initiation or conduction in the myocardial tissue. The term tachycardia is used to describe an excessively rapid heartbeat resulting from repetitive stimulation of the heart muscle. Such disturbances often arise from additional conduction pathways that are present within the heart either from a congenital developmental abnormality or an acquired abnormality, which changes the structure of the cardiac tissue, such as a myocardial infarction.

A common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Atrial arrhythmia may also occur. Three of the most common atrial arrhythmia are ectopic atrial tachycardia, atrial fibrillation, and atrial flutter. Atrial fibrillation can cause significant patient discomfort and even death because of a number of associated problems, including, e.g., an irregular heart rate (which causes patient discomfort and anxiety), loss of synchronous atrioventricular contractions (which compromises cardiac hemodynamics, resulting in varying levels of congestive heart failure) and stasis of blood flow (which increases the likelihood of thromboembolism).

In the past, problems associated with arrhythmia have been treated with pharmacological treatment. Such treatment may not be effective in all patients and is frequently plagued with side effects, including, e.g., dizziness, nausea, vision problems, and other difficulties.

Alternatively, such disturbances are treated by identifying the conductive pathways and then severing part of this pathway by destroying these cells, which make up a portion of the pathway. Traditionally, this has been done by either cutting the pathway surgically; freezing the tissue, thus destroying the cellular membranes; or by heating the cells, thus denaturing the cellular proteins. The resulting destruction of the cells eliminates their electrical conductivity, thus destroying, or ablating, a certain portion of the pathway. By eliminating a portion of the pathway, the pathway may no longer maintain the ability to conduct, and the tachycardia ceases.

Catheters are a common medical tool that has been used for many years. They are employed, e.g., for medical procedures to examine, diagnose, and treat while positioned at a specific location within the body that is otherwise inaccessible without more invasive procedures. In such procedures, a catheter is first inserted into a vessel near the surface of the body and the guided to a specific location within the body. For example, a catheter may be used to convey an electrical stimulus to a selected location within the human body or a catheter with sensing electrodes may be used to monitor various forms of electrical activity in the human body.

Catheters have increasingly become a common medical procedure for the treatment of certain types of cardiac arrhythmia. Catheter ablation is based on the idea that by ablation (i.e., destroying) abnormal tissue areas in the heart, its electrical system can be repaired and the heart will return to a normal rhythm. During catheter ablation, the catheter is typically inserted in an artery or vein in the leg, neck, or arm of the patient and then threaded, sometimes with the aid of a guide wire or introducer, through the vessels until a distal tip of the catheter reaches the desired location for the medical procedure in the heart.

There are a number of methods used for ablation of desired areas, including for example, radiofrequency (RF) ablation. Ablation may be facilitated by transmission of energy from an electrode assembly to ablate tissue at the target site. Because ablation may generate significant heat, which if not controlled can result in excessive tissue damage, such as steam pop, tissue charring, and the like, it is desirable to include a mechanism to irrigate the target area and the device with biocompatible fluids, such as water or saline solution. The use of irrigated ablation catheters can also prevent the formation of soft thrombus and/or blood coagulation.

Irrigated ablation catheters are cooled by passing a fluid through the catheter during ablation. Saline irrigation is an effective way to cool the ablation electrode and keep efficient flow around the electrode to prevent blood coagulation. Furthermore, the surface cooling that results from the saline irrigation reduces heating at the point of highest current density where excessive temperatures would normally produce charring, crater formation and impedance rises (Thomas, et al., *Europace* 6: 330-335 (2004)).

Open irrigated ablation catheters are currently the most common irrigated catheters in the electrophysiology field. Examples of these devices include THERMOCOOL® by Biosense Webster and COOLPATH® by Irvine Biomedical. Closed ablation catheters usually circulate a cooling fluid within the inner cavity or lumen provided by the ablation electrode. Open ablation catheters typically deliver the cooling fluid through open outlets or openings to a surface of the electrode. Open ablation catheters use an inner cavity or lumen of the electrode, as a manifold to distribute saline solution, or other irrigation fluids known to those skilled in the art, to one or more passageways that lead to an opening/outlet provided on the surface of the electrode. The cooling fluid thus flows through the outlets of the passageways onto the electrode member. This flow through the electrode tip lowers the temperature of the tip during operation, often making accurate monitoring and control of the ablative process more difficult.

Using irrigated ablation catheters can prevent the impedance rise of tissue in contact with the electrode, prevent soft thrombus formation, and steam "pop" inside of the tissue while maximizing the potential energy transfer to the tissue, thereby allowing an increase in the lesion size produced by the ablation. Open irrigated ablation catheters can improve the safety of RF ablation by preventing protein aggregation and blood coagulation. However, tissue char is often a problem with irrigated catheters.

BRIEF SUMMARY OF THE INVENTION

The present invention is directed to improved ablation electrode assemblies and methods useful in conjunction with irrigated catheter devices and other ablation catheters, wherein tissue char is minimized during RF ablation. Embodiments of the present invention provide an irrigated catheter having irrigation fluid directed at target areas where coagulation is more likely to occur so as to minimize blood coagulation and associated problems. The present invention includes various embodiments of irrigation electrode assemblies having a passageway for minimizing the blood coagulation and related problems occurring at or about the distal end of the electrode.

Accordingly, the present invention includes an irrigated ablation electrode assembly. The electrode assembly has an outer surface, an inner lumen, and a proximal member. The electrode assembly further includes a distal member having a distal end. The proximal member and distal member are configured for connection with one another. The assembly further includes at least one passageway extending from the inner lumen to the outer surface of the assembly. The at least one passageway from the inner lumen to the outer surface has a smooth conjunction, wherein the smooth conjunction comprises a rounded edge or is chamfered. If the conjunction comprises a rounded edge, the rounded edge can have a fixed radius. The fixed radius can be, for example, from about 0.002" to about 0.008". The chamfer has a width of the cut surface, from about 0.001" to 0.004". The chamfer has a width of the cut surface, from about 0.001" to about 0.004".

The present invention includes an alternate embodiment of an irrigated ablation electrode assembly. The electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. At least one of the distal or proximal passageways from the inner lumen to the outer surface of the proximal and/or distal member has a smooth conjunction, wherein the smooth conjunction comprises a rounded edge or is chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". In an embodiment, the proximal passageway is separated from and does not come in contact with the distal member.

The present invention further includes an alternate embodiment of an irrigated ablation electrode assembly. In an alternate embodiment, the electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. At least one of the distal or proximal passageways from the inner lumen to the outer surface of the proximal and/or distal member has a smooth conjunction, wherein the smooth conjunction comprises a rounded edge or is chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". According to the alternate embodiment, the proximal member has a lower thermal conductivity than the distal member.

The present invention further includes an alternate embodiment of an irrigated ablation electrode assembly. In an alternate embodiment, the electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. At least one of the distal or proximal passageways from the inner lumen to the outer surface of the proximal and/or distal member has a smooth conjunction, wherein the smooth conjunction comprises a rounded edge or is chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". The assembly further includes an insulating member at least partially separating the distal passageway from the distal member, wherein the insulating member has a lower thermal conductivity than the distal member.

The present invention further includes an alternate embodiment of an irrigated ablation electrode assembly. In an alternate embodiment, the electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. At least one of the distal or proximal passageways from the inner lumen to the outer surface of the proximal and/or distal member has a smooth conjunction, wherein the smooth conjunction comprises a rounded edge or is chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". In accordance with an alternate embodiment, the inner lumen includes a hydrophilic coating.

The foregoing and other aspects, features, details, utilities, and advantages of the present invention will be apparent from reading the following description and claims, and from reviewing the accompanying drawings.

DETAILED DESCRIPTION OF THE INVENTION

The inventors solved the problem of undesirable tissue charring during RF ablation by providing irrigation holes that lead from the inner cavities of electrodes that have smooth or chamfered conjunctions with the outer surface of the electrode of irrigated ablation catheters. The inventors observed that commercially available, irrigated RF catheters often caused tissue char during ablation. While not desiring to be bound by any particular theory, careful observation from the inventors led them to believe that the rough edges of the irrigation holes were partly responsible for tissue char, wherein the rough edges were responsible for a concentration of energy intensity ("edge effects").

In general, the instant invention relates to irrigated ablation electrode assemblies, to catheter assemblies, as well as ablation systems employing the irrigated ablation electrode assemblies, 110, 10 and 10', in connection with catheter assemblies. For purposes of this description, similar aspects among the various embodiments described herein will be referred to by the same reference number. As will be appreciated, however, the structure of the various aspects may differ with respect to alternate embodiments.

Figure 2:
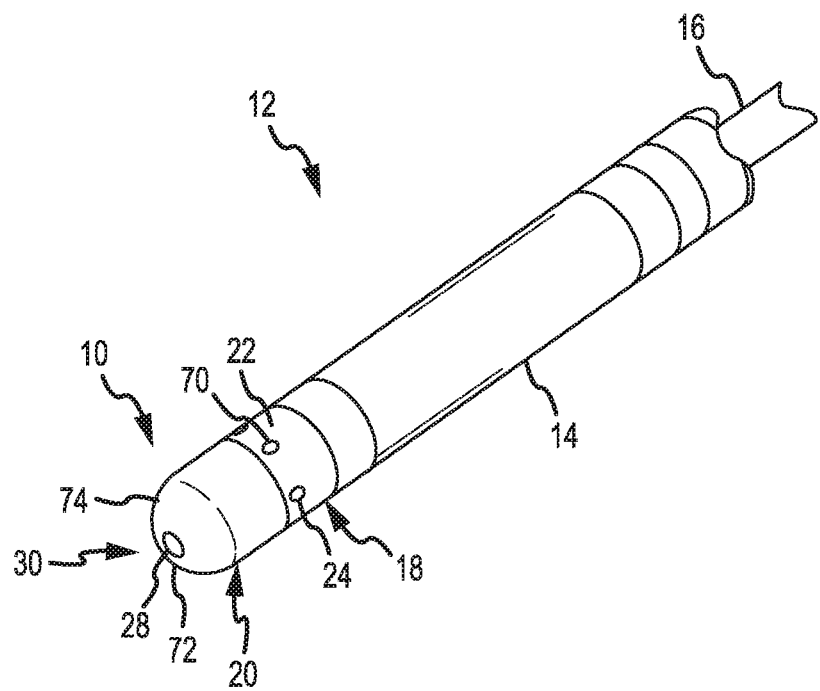
FIG. 2 is an isometric view of an ablation electrode according to an embodiment of the present invention.

As generally shown in the embodiment illustrated in FIG. 2, the ablation electrode assembly 10 may comprise part of an irrigated ablation catheter assembly 12. The embodiments describe RF ablation electrodes and assemblies, but it is contemplated that the present invention is equally applicable to any number of other ablation electrodes and assemblies where the temperature of the device and the targeted tissue area may be factors during the procedure.

Figure 1A:
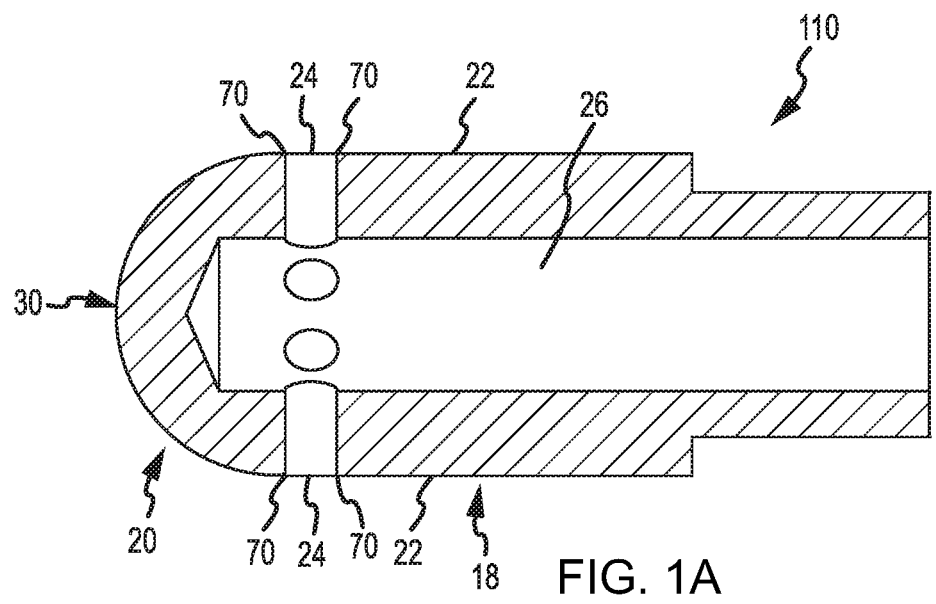
FIGS. 1A (prior art), 1B, 1C, and 1D are cross-sectional views of an ablation electrode.

FIG. 1A shows a prior art configuration of an ablation electrode. The ablation electrode has an electrically conductive electrode 110 that includes a proximal member 18, also referred to as an irrigation member or manifold, and a distal member 20, also referred to as an ablation electrode member. The orientation of members 18, 20 are generally such that distal member 20, which provides an ablation electrode or an ablative surface, is situated at the distal end of assembly 110. Proximal member 18 includes an outer surface 22. Proximal member 18 further includes at least one fluid or irrigation passageway 24, also referred to as proximal passageway 24, that extends from an inner lumen 26, to outer surface 22 of proximal member 18. In prior art configurations, the conjunction 70 of the irrigation passageway 24 with the outer surface 22 of the proximal member is rough. Inner lumen 26 is in fluid communication with a fluid delivery tube (not shown). Fluid passageways 24 of proximal member 18 and distal passageway 28 (FIG. 2) allow for increased irrigation of electrode assembly 110 during the ablation of tissue.

Figure 1B:
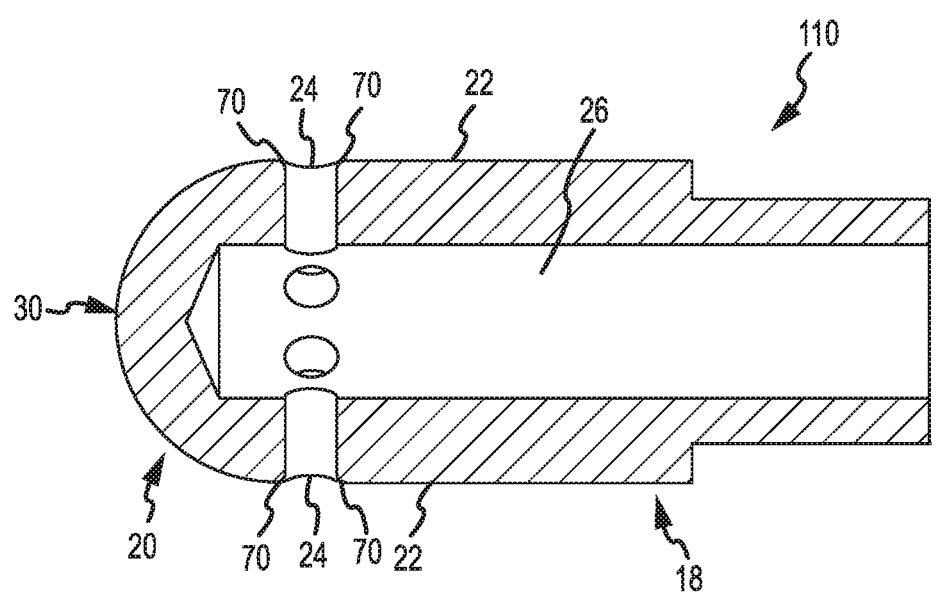

FIG. 1B shows the improvement of the present invention. As in FIG. 1A, the ablation electrode has an electrically conductive electrode 110 includes a proximal member 18, also referred to as an irrigation member or manifold, and a distal member 20, also referred to as an ablation electrode member. The orientation of members 18, 20 are generally such that distal member 20, which provides an ablation electrode or an ablative surface, is situated at the distal end of assembly 110. Proximal member 18 includes an outer surface 22. Proximal member 18 further includes at least one fluid or irrigation passageway 24, also referred to as proximal passageway 24, that extends from an inner lumen 26, to outer surface 22 of proximal member 18. The conjunction 70 of the irrigation passageway 24 with the outer surface 22 of the proximal member 18 is smooth or chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". Inner lumen 26 is in fluid communication with a fluid delivery tube (not shown). Fluid passageways 24 of proximal member 18 and distal passageway 28 allow for increased irrigation of electrode assembly 110 during the ablation of tissue.

Figure 1C:
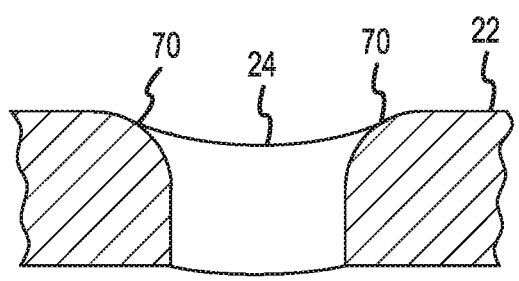

The smooth conjunction 70 is shown to closer advantage in FIG. 1C, showing an irrigation pathway 24 and the outer surface 22 of the proximal member 18. Smooth conjunction 70 can have a fixed radius. In one embodiment, the fixed radius is about 0.002" to 0.008". In other embodiments, the fixed radius is about 0.002", about 0.003", about 0.004", about 0.005", about 0.006", about 0.007", and about 0.008".

Figure 1D:
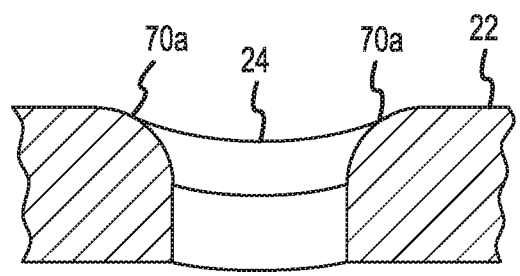

FIG. 1D shows another solution to minimize the edge effect, showing instead of a smooth conjunction 70, a chamfered conjunction 70*a*. Also shown is irrigation pathway 24 and the outer surface 22 of the proximal member.

In accordance with another embodiment, FIG. 2 illustrates an ablation electrode assembly 10 connected to catheter shaft 14 as part of irrigated ablation catheter assembly 12. The assembly 12 includes at least one fluid delivery tube 16. Ablation electrode assembly 10 includes a proximal member 18, also referred to as an irrigation member or manifold, and a distal member 20, also referred to as an ablation electrode member. Proximal member 18 and distal member 20 are configured to be connected together. The orientation of members 18, 20 are generally such that distal member 20, which provides an ablation electrode or an ablative surface, is situated at the distal end of assembly 10. Proximal member 18, or irrigation member, is located at the proximal end of assembly 10, although for some embodiments the orientation could be reversed.

Figure 3:
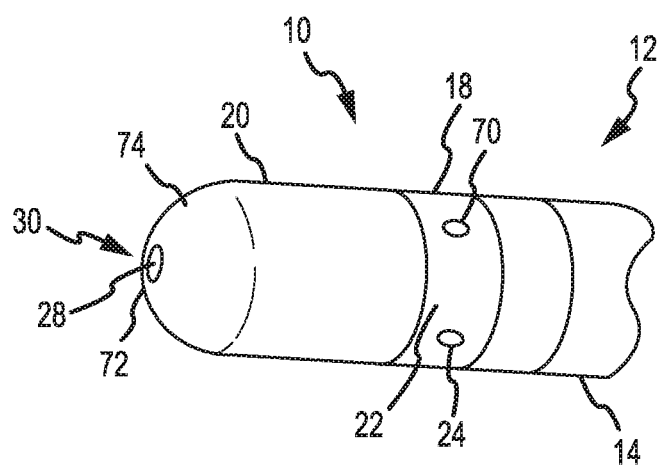
FIG. 3 is an enlarged isometric view of the distal end of the ablation electrode as shown in FIG. 2.

Proximal member 18 includes an outer surface 22. Proximal member 18 further includes at least one fluid or irrigation passageway 24, also referred to as proximal passageway 24, that extends from an inner lumen 26, for example as generally shown in FIGS. 6, 7A, 7B, and 8, to outer surface 22 of proximal member 18. The conjunction 70 of the irrigation passageway 24 with the outer surface 22 of the proximal member 18 is smooth or chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". Inner lumen 26 is in fluid communication with fluid delivery tube 16. As can be further seen in FIGS. 3-5, distal member 20 includes a distal passageway 28 that extends to distal end 30 of electrode assembly 10. Fluid passageways 24 of proximal member 18 and distal passageway 28 allow for increased irrigation of electrode assembly 10 during the ablation of tissue. The conjunction 72 of the distal passageway 28 with the outer surface 74 of the distal member 20 is smooth or chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". Proximal passageway 24 is separated from and does not come in contact with distal member 20.

Figure 4:
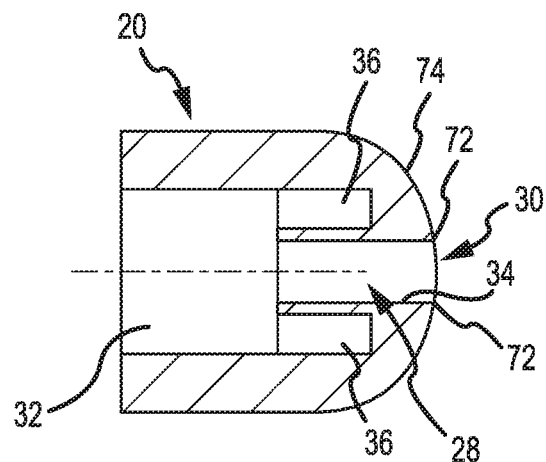
FIG. 4 is a side cross-sectional view of a distal member of an ablation electrode according to an alternate embodiment of the present invention.
Figure 5:
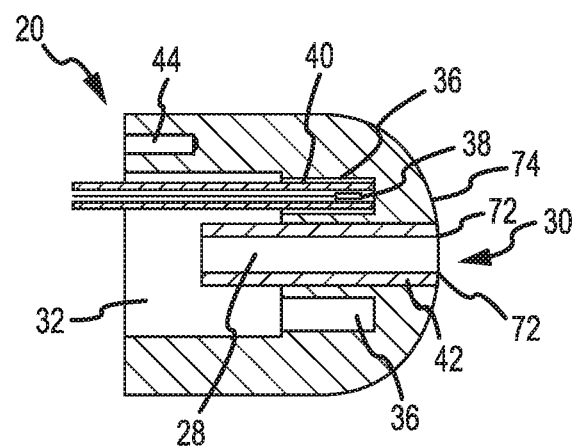
FIG. 5 is a side cross-sectional view of a distal member of an ablation electrode according to an alternate embodiment of the present invention.

Distal member 20, as shown in FIGS. 4 and 5, is generally comprised of an electrically, and potentially thermally, conductive material known to those of ordinary skill in the art for delivery of ablative energy to target tissue areas. Examples of electrically conductive material include gold, platinum, iridium, palladium, stainless steel, and various mixtures and combinations thereof. In an embodiment, the distal member may be hemispherical or semispherical in shape, although other configurations may be used.

Distal member 20 may further include an inner cavity 32 for receiving a portion of proximal member 18, as further discussed below. Distal member 20 further includes an aperture 34 therein forming distal passageway 28. Aperture 34 extends through distal member 20 to distal end 30 therein providing an opening or outlet for distal passageway 28 on the surface of distal member 20. Distal member 20 may further be configured with one or more component cavities 36 for receiving and/or housing additional components within distal member 20.

As can be seen in FIG. 5, at least one temperature sensor 38, also referred to as a temperature or thermal sensing device, may be provided within a portion (e.g., cavity 36) of distal member 20. In an alternate embodiment, two temperature sensors may be provided within cavities 36 of distal member 20. Various configurations of distal member 20 may include temperature sensor 38 in different locations and proximities within distal member 20. In an alternate embodiment, the temperature sensor 38 may be either partially or completely surrounded by or encapsulated by an insulation liner that is made of thermally conductive and electrically non-conductive materials. Insulation liner 40 may be provided in various configurations, such as provided by a tube-like configuration, as shown in FIG. 5. Liner 40 may be comprised of various materials, such as for example polyimide tubing.

As generally illustrated in FIG. 5, distal member 20, may further include an insulating member 42, i.e. thermal liner, disposed within aperture 34, forming distal passageway 28 of distal member 20. Insulating member 42 may be comprised of a non and/or poor thermally conductive material. Such material may include, but is not limited to, high-density polyethylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof. Insulating member 42 may be generally provided in a configuration that reflects the size and shape of aperture 34, although the insulating member 42 generally extends to meet and connect to inner lumen 26 of proximal member 18. Distal passageway 28 is therein created for the flow of fluid from proximal member 18, for example, as generally shown in FIGS. 6, 7A, 7B, and 8, through distal passageway 28 to distal end 30 of assembly 10.

An alternate embodiment of distal member 20 includes a cavity 44 for receiving a power wire 46 (see, e.g., FIGS. 6, 7A, 7B, and 8) for connecting distal member 20 to an energy source, such as an RF energy source. In an alternate embodiment, cavity 44 may further include a non and/or poor thermally conductive material. Furthermore, in an alternate embodiment, power wire 46 may be soldered directly to distal member 20, or attached and/or connected to distal member 20 through the use of an adhesive or any other connection method known to one of ordinary skill in the art.

FIGS. 6, 7A, 7B, and 8 generally illustrate alternate embodiments of electrode assembly 10, 10' of the present invention. As previously described, proximal member 18, 18' and distal member 20 are configured to be connected and/or coupled together with one another. Proximal member 18, 18' is comprised of a thermally nonconductive or reduced (i.e. poor) thermally conductive material that serves to insulate the fluid from the remaining portions of electrode assembly 10, in particular distal member 20. Moreover, proximal member 18, 18' may comprise an electrically nonconductive material. Comparatively, overall, proximal member 18, 18' may have lower thermal conductivity than distal member 20. In an embodiment, proximal member 18, 18' is made from a reduced thermally conductive polymer. A reduced thermally conductive material is one with physical attributes that decrease heat transfer by about 10% or more, provided that the remaining structural components are selected with the appropriate characteristics and sensitivities to maintain adequate monitoring and control of the process. One reduced thermally conductive material may include polyether ether ketone ("PEEK"). Further examples of reduced thermally conductive materials useful in conjunction with the present invention include, but are not limited to, high-density polyethylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof. Moreover, proximal member 18 is substantially less thermally conductive than distal member 20. As a result, the irrigation fluid flowing through proximal member 18 has very little thermal effect on distal member 20 due to the poor thermal conductivity of proximal member 18 (e.g., less than 5% effect), and preferably nearly 0% effect. In general, characteristics and descriptions (e.g., composition and materials) regarding proximal member 18 and 18' may be used interchangeably, among various embodiments except for the specific descriptions provided regarding the design of proximal member 18' in accordance with the embodiment provided in FIG. 8.

The proximal member 18 may further be configured to include a coupling portion 48 that extends into inner cavity 32 of distal member 20. Proximal member 18 may be generally cylindrical in shape. Moreover, for some embodiments, distal member 20 of ablation electrode assembly 10 may have a generally cylindrical shape terminating in a hemispherical distal end 30. The cylindrical shape of proximal member 18 and distal member 20 may be substantially similar to one another and generally have the same overall diameter, which can provide or create a smooth outer body or profile for electrode assembly 10. Distal member 20 may be configured to accept portion 48 of proximal member 18 for attachment thereto. The distal member 20 may be connected by any known mechanism including adhesives, press-fit configurations, snap-fit configurations, threaded configurations, or any other mechanism known to one of ordinary skill in the art.

Proximal member 18 may further include an inner lumen 26 that is connected to fluid delivery tube 16. The inner lumen 26 may act as a manifold or distributor for transporting and/or distributing fluid throughout electrode assembly 10. In particular, proximal member 18 may be configured to receive a fluid delivery tube 16 carried within at least a portion of catheter assembly 12. Proximal member 18 includes a plurality of passageways 24. Proximal member 18 may serve as a manifold or distributor of fluid to electrode assembly 10 through the use of passageways 24. Proximal passageways 24 may extend from inner lumen 26 axially toward outer surface 22 of proximal member 18, wherein the conjunction 70 of the irrigation passageway 24 with the outer surface 22 of the proximal member 18 is smooth or chamfered. If the conjunction comprises a rounded edge, the rounded edge can have a fixed radius. The fixed radius can be, for example, from about 0.002" to about 0.008". The chamfer has a width of the cut surface, from about 0.001" to about 0.004". In an embodiment, a plurality of passageways 24 are substantially equally distributed around proximal member 18 to provide substantially equal distribution of fluid to the targeted tissue area and/or the outside of electrode assembly 10. Electrode assembly 10 may be configured to provide a single, annular passageway 24, or a number of individual passageways 24 equally distributed around the proximal member 18. Moreover, the passageways 24 may be generally tubular and may have a constant diameter along the length of the passageway. Alternate configurations having various diameters along all or portions of the length of the passageways may be used.

As shown in FIGS. 6, 7A, 7B and 8, proximal passageways 24 may be directed towards or extend towards distal member 20 of electrode assembly 10 at an angle (Θ) less than 90 degrees from the central longitudinal axis of proximal member 18. In an embodiment, passageways 24 extends at an angle (Θ) between about 20 to about 70 degrees, and for some embodiments, between about 30 to about 60 degrees. Alternate positions and angles of the passageway(s) 24 may be provided in alternate embodiments of electrode assembly 10.

Figure 6:
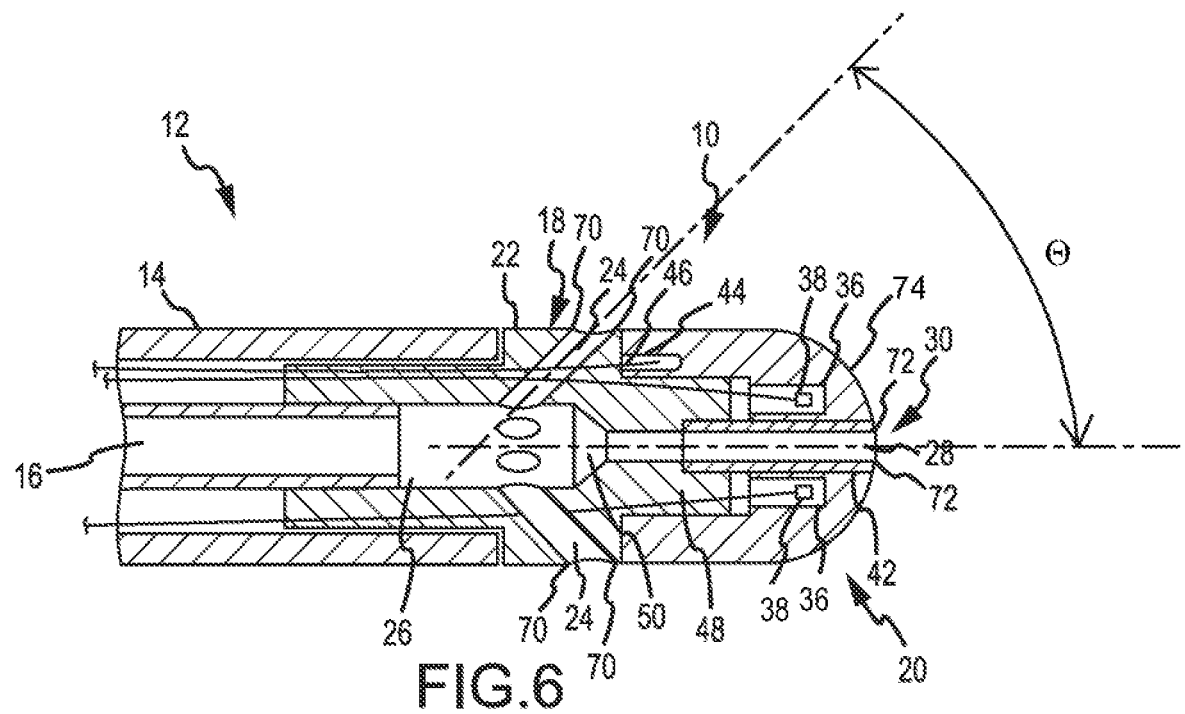
FIGS. 6, 7A, 7B, and 8 are side cross-sectional views of ablation electrodes according to alternate embodiments of the present invention.
Figure 7A:
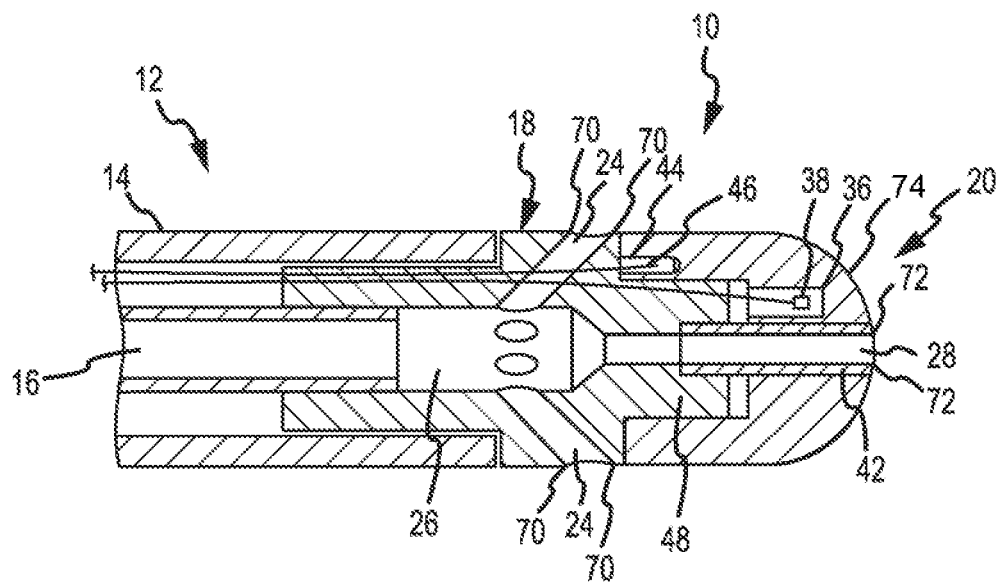
Figure 7B:
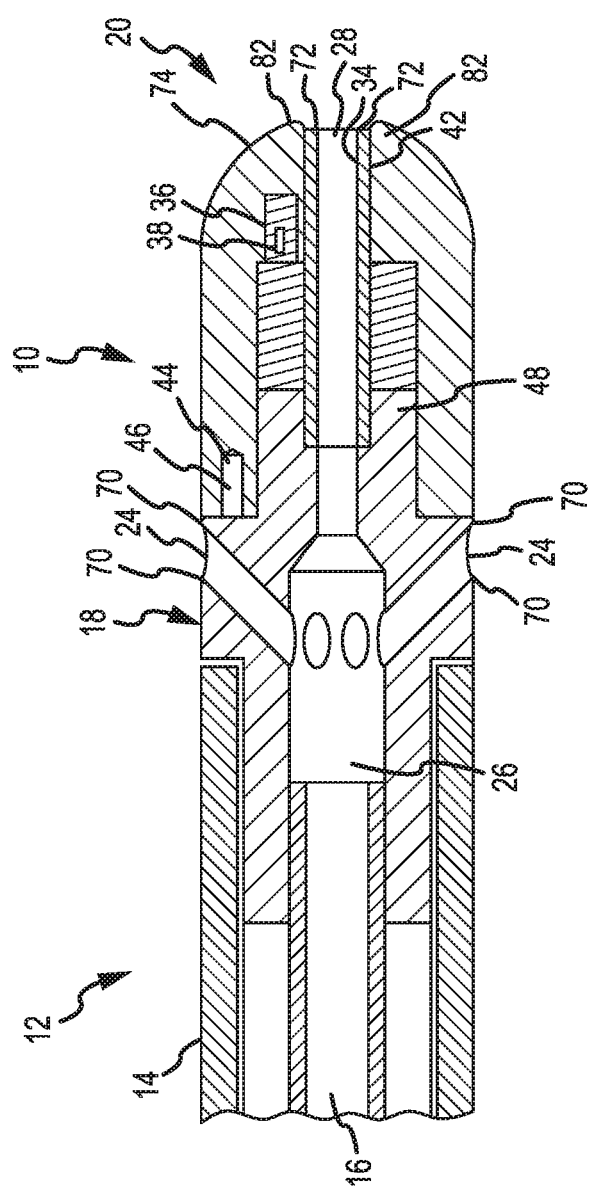

Distal passageway 28 is provided for and extends along the central longitudinal axis of proximal member 18 through distal member 20 to distal end 30 of electrode assembly 10. As shown in FIGS. 6, 7A, and 7B, distal passageway 28 may further be fully or partially surrounded by a thermally non-conductive material, such as that provided by insulating member 42. Insulating member 42 prevents saline or any other biocompatible fluid from coming in contact with distal member 20. Insulating member 42 may be comprised of a thermally non-conductive material such as, but not limited to, high-density polyethylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof.

Distal passageway 28 extends from inner lumen 26 provided by proximal member 18. In general, the diameter of distal passageway 28 is less than the diameter of inner lumen 26 of proximal member 18. Accordingly, in one embodiment, inner lumen 26 and distal passageway 28 may be connected by a tapered transition portion 50 therein providing constant fluid communication. The angle of the tapered transition portion may vary depending on the diameters of the inner lumen 26 and distal passageway 28, as well as the length of proximal member 18. The presence of the tapered transition portion 50 between inner lumen 26 and distal passageway 28 prevents air bubbles from being trapped inside the proximal member during fluid flow through the lumen and passageways. In an embodiment, distal passageway 28 is slightly larger in diameter than passageways 24 provided by the proximal member. The diameter of passageways 24 and distal passageways 28 may vary depending on the configuration and design of electrode assembly 10. In an embodiment, distal passageway 28 includes a diameter within the range of about 0.012 to about 0.015 inches, more particularly about 0.013 to about 0.014 inches. In another embodiment, proximal passageways 24 include a diameter within the range of about 0.011 to about 0.014 inches, more particularly about 0.011 to about 0.013 inches.

In another embodiment, the inner surface of inner lumen 26 may be either coated with a hydrophilic coating or surface treated to create a hydrophilic surface. The treatment of inner lumen 26 with a hydrophilic surface or coating results in another method of preventing air bubbles from becoming trapped inside proximal member 18. The hydrophilic coating materials may include, but are not limited to, block copolymers based of ethylene oxide and propylene oxide, polymers in the polyethylene glycol family and silicone. For example, those materials selected from the group including PLURONIC® from BASF, CARBOWAX® from Dow Chemical Company and SILASTIC MDX® from Dow Corning.

Alternate embodiments of the present invention provide the incorporation of at least one temperature sensor 38 in combination with distal passageway 28. In particular, an embodiment, as shown in FIG. 6, includes two temperature sensors 38 provided within cavities 36 of distal member 20. In an alternate embodiment, as shown in FIG. 7A, one temperature sensor is provided within a single cavity 36. Temperature sensors may include various temperature sensing mechanisms, such as a thermal sensor, disposed therein for measurement and control of electrode assembly 10. The temperature sensor 38 can be any mechanism known to one of skill in the art, including for example, thermocouples or thermistors. The temperature sensor 38 may further be surrounded, or encapsulated, by a thermally conductive and electrically non-conductive material, as previously discussed. This thermally conductive and electrically non-conductive material can serve to hold temperature sensor 38 in place within distal member 20 and provide improved heat exchange between temperature sensor 38 and distal member 20. This material may be comprised of a number of materials known to one of ordinary skill in the art, including for example, thermally conductive resins, epoxies, or potting compounds. In yet another alternate embodiment, as shown in FIG. 7B, the distal passageway hole has rounded edges 82.

Figure 8:
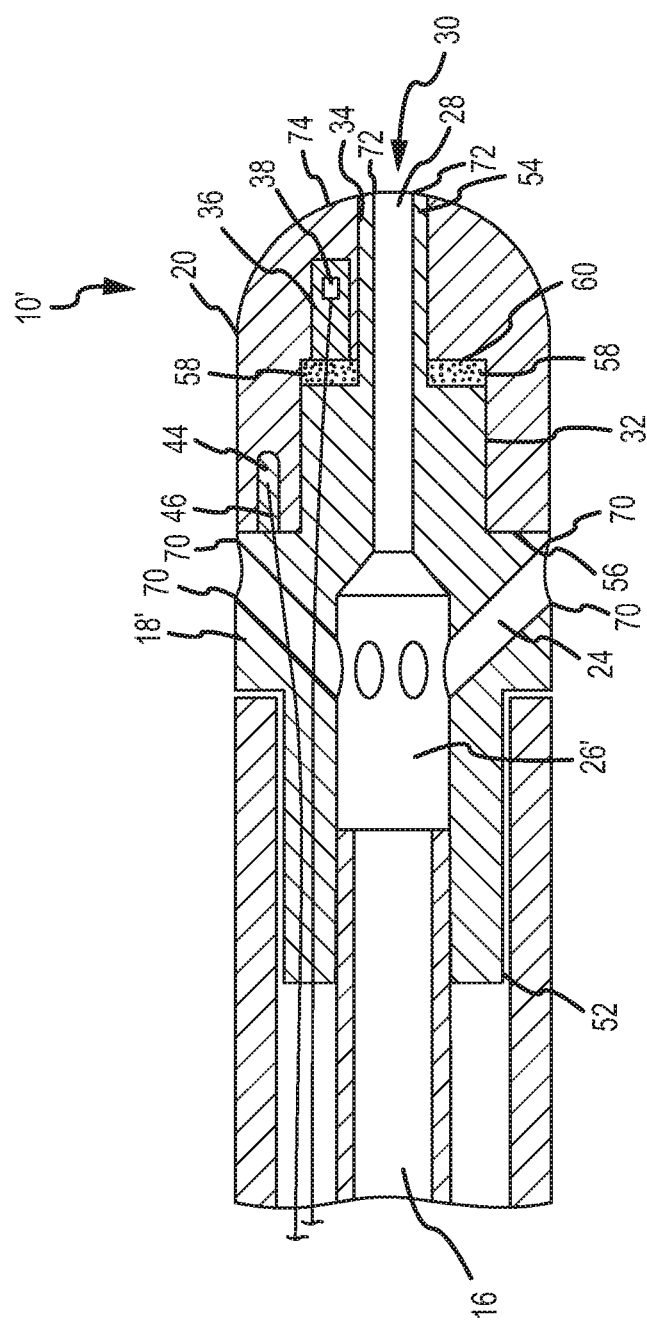

In another embodiment of electrode assembly 10', as seen in FIG. 8, proximal member 18' includes proximal end 52 and an extended distal end 54 that is received within aperture 34 of distal member 20 when proximal member 18' and distal member 20 are configured for connection. Distal member 20 provides a proximal surface 56 and the surface 60 provided by inner cavity 32 that may be connected to proximal member 18' through the use of bonding or adhesive 58, therein coupling and/or connecting proximal member 18' with distal member 20. Inner lumen 26' extends from proximal end 52 to distal end 54 of proximal member 18'. Accordingly proximal member 18' is configured to provide the insulating portion of distal passageway 28 through distal member 20. As a result, the non-thermally conductive material of the proximal member, as previously described above, insulates distal passageway 28 through distal member 20. Proximal member 18' further includes proximal passageways 24, as described above, that allow fluid flow from inner lumen 26' to outer surface 22' of proximal member 18'. Passageways 24 are directed towards distal member 20 to increase the fluid flow around the intersection of the proximal member to the distal member.

Figure 9:
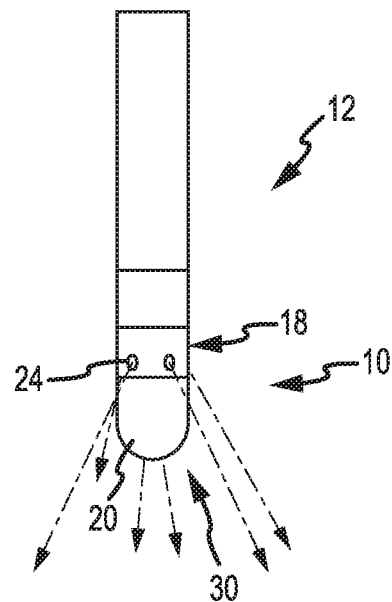
FIG. 9 is an illustrative view of visualized irrigation flow from an ablation electrode according to an alternate embodiment of the present invention.

The flow of fluid through inner lumen 26' provided by fluid tube 16 and ultimately through proximal passageways 24 and distal passageway 28 is reflected in FIG. 8. In particular, FIG. 9 provides an irrigation flow visualization wherein the fluid from proximal passageways 24 is directed at a 30 degree angle from the central longitudinal axis of proximal member 18, as shown in FIG. 8. The flow visualization further shows the flow of fluid out of distal passageway 28, as shown in FIGS. 6-8, from distal end 30 of electrode assembly 10'.

Figure 10:
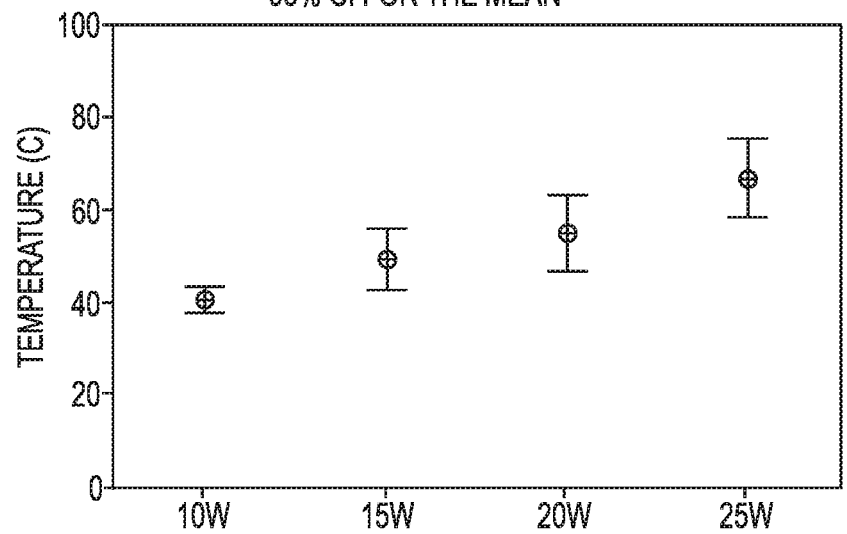
FIG. 10 graphically depicts general bench test results for ablation electrode assemblies in accordance with an embodiment of the present invention.

FIG. 10 graphically depicts bench test results for ablation electrode assemblies in accordance with an embodiment of the present invention. The purpose of the testing was to confirm that adequate temperature control was being accomplished through the use of the irrigated electrode including a distal passageway as the ablation system was subjected to an overall increase in power (W) (e.g., wattage). Overall, the testing was performed using an embodiment of the present invention wherein ablation was being performed using an electrode assembly that maintained irrigation flow of fluid was 13 mL/M at a perpendicular orientation to the muscle tissue being ablated. The testing showed, as reflected in FIG. 10, that an adequate temperature response was exhibited by the ablation electrode assembly, upon the continued increase of power (W) provided to the ablation system. Overall, the ablation electrode, as provided by the present invention, having a distal irrigation passageway was able to maintain adequate temperature control, for performing ablation, while at the same time sufficiently cooling the electrode tip. Accordingly, it is desirable to provide an irrigated ablation electrode assembly in accordance with the present invention that can achieve adequate temperature response within a desired range for performing ablation procedures.

As previously discussed, the ablation electrode assembly 10, 10', 110 of the present invention may comprise part of an irrigated ablation catheter assembly 12, operably connected to a pump assembly and an RF generator assembly which serves to facilitate the operation of ablation procedures through monitoring any number of chosen variables (e.g., temperature of the ablation electrode, ablation energy, and position of the assembly), assist in manipulation of the assembly during use, and provide the requisite energy source delivered to the electrode assembly 10, 10', 110. Although the present embodiments describe RF ablation electrode assemblies and methods, it is contemplated that the present invention is equally applicable to any number of other ablation electrode assemblies where the temperature of the device and the targeted tissue areas is a factor during the procedure.

In addition to the preferred embodiments discussed above, the present invention contemplates methods for improved measure and control of a temperature of an irrigated ablation electrode assembly 10, 10', 110 or a target site and minimization of coagulation and excess tissue damage at and around the target site. According to one method, an ablation electrode assembly 10, 10', 110 is provided, having at least one temperature sensor 38 within distal member 20 and proximal member 18 is separate from distal member 20. An irrigation pathway 24 is provided within the proximal member 18 for delivery of fluid to the outer surface 22 of the proximal member 18. A distal passageway 28 is further provided for delivery of fluid to the distal end of distal member 20, thereby allowing for the benefits of irrigation of the target site and external portions of electrode assembly 10, such as minimizing tissue damage, such as steam pop, preventing rising impedance of the ablation assembly, and minimizing blood coagulation.

Other embodiments and uses of the devices and methods of the present invention will be apparent to those skilled in the art from consideration of the specification and practice of the invention disclosed herein. The specification and examples should be considered exemplary only with the true scope and spirit of the invention indicated by the following claims. Although a number of embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claim.

What is claimed is:

1. An irrigated ablation electrode assembly comprising:
a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the passageway; and
at least one temperature sensor mounted in at least one of the plurality of longitudinally extending component cavities;
wherein the fluid passageway terminates in an aperture through the distal member and the distal member outer surface; and
wherein a conjunction of the fluid passageway and the distal member outer surface is rounded or chamfered and is configured to reduce energy intensity concentration at the conjunction.

2. An irrigated ablation electrode assembly comprising:
a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the passageway; and
at least one temperature sensor mounted in at least one of the plurality of longitudinally extending component cavities;
wherein the fluid passageway extends axially along a central longitudinal axis of the distal member to the distal member outer surface; and
wherein a conjunction of the fluid passageway and the outer surface is chamfered, the chamfer having a width of a cut surface from about 0.001 inches to about 0.004 inches, and the conjunction being configured to reduce energy intensity concentration at the conjunction.

3. An irrigated ablation electrode assembly comprising:
a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the passageway; and
at least one temperature sensor mounted in at least one of the plurality of longitudinally extending component cavities;
wherein the fluid passageway extends axially along a central longitudinal axis of the distal member to the distal member outer surface; and
wherein a conjunction of the fluid passageway and the outer surface is rounded, the conjunction having a radius of about 0.002" to about 0.008", and the conjunction being configured to reduce energy intensity concentration at the conjunction.

4. An irrigated ablation electrode assembly comprising:
a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the passageway;
at least one temperature sensor mounted in at least one of the plurality of longitudinally extending component cavities; and
a proximal member comprising a proximal member outer surface, an inner lumen, and a proximal fluid passageway extending radially outwardly from the inner lumen to the proximal member outer surface,
wherein a conjunction of the proximal fluid passageway and the proximal member outer surface is rounded or chamfered and reduces energy intensity concentration at the conjunction.

5. An irrigated ablation electrode assembly comprising:
a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the fluid passageway and terminating in the distal member, wherein said plurality of longitudinally extending component cavities comprises a first component cavity and a second component cavity; and
a plurality of temperature sensors terminating in the plurality of longitudinally extending component cavities in the distal member, wherein the plurality of temperature sensors comprises a first temperature sensor terminating in the first component cavity, and a second temperature sensor terminating in the second component cavity;

wherein the fluid passageway terminates in an aperture through the distal member and the distal member outer surface; and wherein a conjunction of the fluid passageway and the distal member outer surface is rounded or chamfered and is configured to reduce energy intensity concentration at the conjunction.

6. An irrigated ablation electrode assembly comprising:

a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the fluid passageway and terminating in the distal member, wherein said plurality of longitudinally extending component cavities comprises a first component cavity and a second component cavity; and a plurality of temperature sensors terminating in the plurality of longitudinally extending component cavities in the distal member, wherein the plurality of temperature sensors comprises a first temperature sensor terminating in the first component cavity, and a second temperature sensor terminating in the second component cavity;

wherein the fluid passageway extends axially along a central longitudinal axis of the distal member to the distal member outer surface; and wherein a conjunction of the fluid passageway and the outer surface is chamfered, the chamfer having a width of a cut surface from about 0.001 inches to about 0.004 inches, and the conjunction being configured to reduce energy intensity concentration at the conjunction.

7. An irrigated ablation electrode assembly comprising:

a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the fluid passageway and terminating in the distal member, wherein said plurality of longitudinally extending component cavities comprises a first component cavity and a second component cavity; and a plurality of temperature sensors terminating in the plurality of longitudinally extending component cavities in the distal member, wherein the plurality of temperature sensors comprises a first temperature sensor terminating in the first component cavity, and a second temperature sensor terminating in the second component cavity;

wherein the fluid passageway extends axially along a central longitudinal axis of the distal member to the distal member outer surface; and wherein a conjunction of the fluid passageway and the outer surface is rounded, the conjunction having a radius of about 0.002" to about 0.008", and the conjunction being configured to reduce energy intensity concentration at the conjunction.

8. An irrigated ablation electrode assembly comprising:

a distal member constructed from an electrically conductive material and comprising the following:
an inner cavity;
a distal end;
an outer surface configured for delivery of ablative energy;
a fluid passageway extending from the inner cavity to the outer surface of the distal member; and
a plurality of longitudinally extending component cavities distributed around the fluid passageway and terminating in the distal member, wherein said plurality of longitudinally extending component cavities comprises a first component cavity and a second component cavity; and a plurality of temperature sensors terminating in the plurality of longitudinally extending component cavities in the distal member, wherein the plurality of temperature sensors comprises a first temperature sensor terminating in the first component cavity, and a second temperature sensor terminating in the second component cavity;

a proximal member including a central longitudinal axis and comprising a proximal member outer surface, an inner lumen, and a proximal fluid passageway extending radially outwardly from the inner lumen to the proximal member outer surface;

wherein a conjunction of the proximal fluid passageway and the proximal member outer surface is rounded or chamfered and reduces energy intensity concentration at the conjunction.

* * * * *